US00RE34513E

United States Patent [19]

Ellner

[11] E Patent Number: Re. 34,513

[45] Reissued Date of Patent: Jan. 18, 1994

[54] ULTRAVIOLET LIQUID PURIFICATION SYSTEM

[75] Inventor: Sidney Ellner, Hartsdale, N.Y.

[73] Assignee: Katadyn Systems, Inc., Mount Kisco, N.Y.

[21] Appl. No.: 748,338

[22] Filed: Aug. 21, 1991

Related U.S. Patent Documents

Reissue of:

[64] Patent No.: 4,103,167
Issued: Jul. 25, 1978
Appl. No.: 714,777
Filed: Aug. 16, 1976

[51] Int. Cl.[5] ..... G01N 21/01

[52] U.S. Cl. ..... 250/432 R; 250/365; 250/373

[58] Field of Search ..... 250/372, 373, 461.1, 250/364, 365, 431, 432 R, 436

[56] References Cited

U.S. PATENT DOCUMENTS

| | | | |
|---|---|---|---|
| 1,208,830 | 12/1916 | Pratt | 250/373 |
| 2,667,584 | 1/1954 | Rhodes | 250/430 |
| 3,182,193 | 5/1965 | Ellner et al. | 250/430 |
| 3,462,597 | 8/1969 | Young | 250/431 |
| 3,471,693 | 10/1969 | Veloz | 250/432 R |
| 3,562,520 | 2/1971 | Hippen | 250/372 |
| 3,566,105 | 2/1971 | Wiltroute et al. | 250/373 |
| 3,634,025 | 1/1972 | Landry | 250/372 |
| 3,948,772 | 4/1976 | Ellner | 210/96.11 |

*Primary Examiner*—Paul M. Dzierzynski
*Assistant Examiner*—James Beyer
*Attorney, Agent, or Firm*—Miller & Christenbury

[57] ABSTRACT

An ultraviolet liquid purification system includes a purification chamber having banks of ultraviolet lamps distributed therein for applying germicidal ultraviolet radiation to the liquid flowing through in said chamber. Ultraviolet photocell detectors are located in said chamber to detect the level of ultraviolet radiation transmitted through the quartz jacket housing the ultraviolet lamps and through the liquid being purified. Indicator means produce an alarm signal when the total ultraviolet radiation transmitted through the liquid drops below a preselected level. In addition, a light conducting fiber is provided for each ultraviolet lamp having its input endface located at the ultraviolet lamp and its output endface at a display panel whereby identification of a particular ultraviolet lamp that has failed may be easily detected. Photocell detector means are provided to detect the light output at the output endface of the light conductor fiber and to produce an alarm signal when said light output fails. An in-place cleaning system for cleaning the interior of the purification chamber is also provided.

13 Claims, 3 Drawing Sheets

FIG. 1
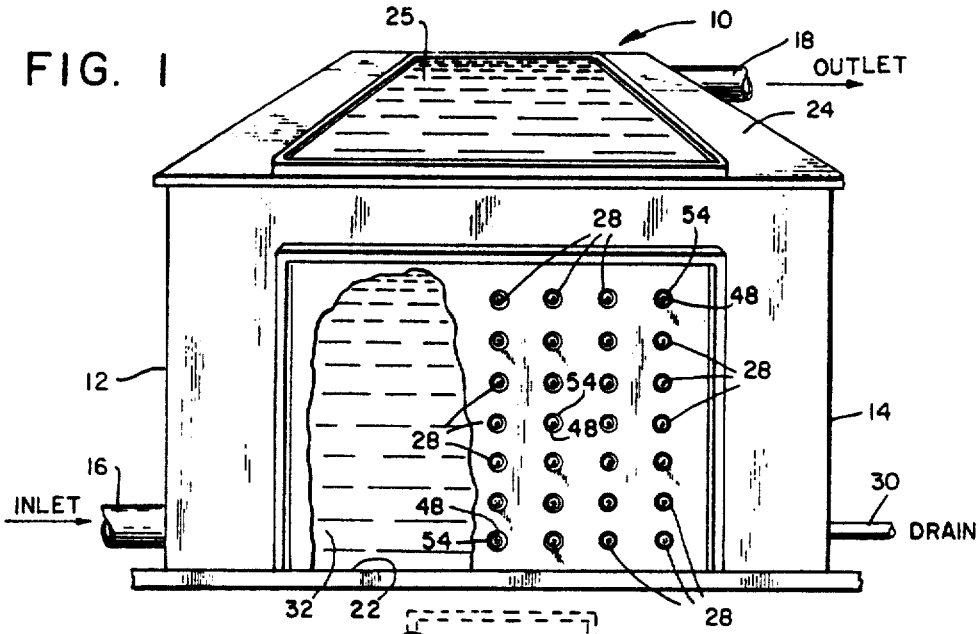
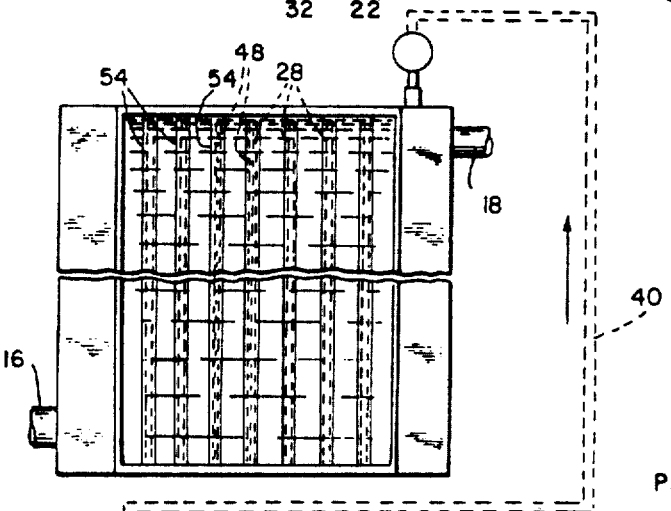
FIG. 2A
FIG. 3A
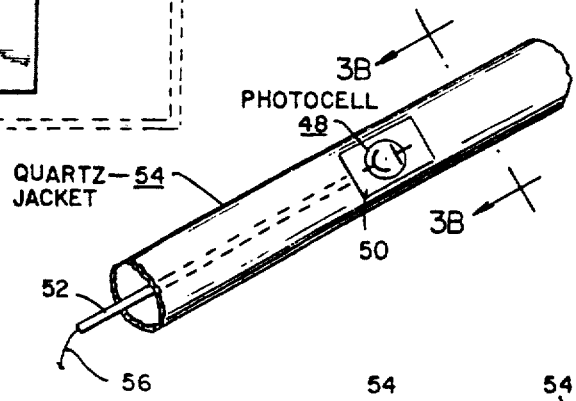
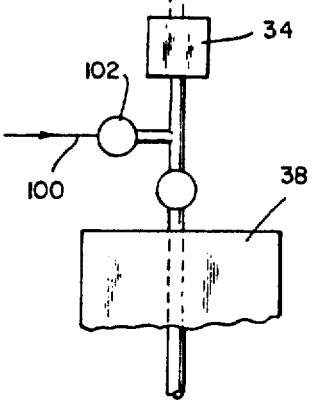
FIG. 3B
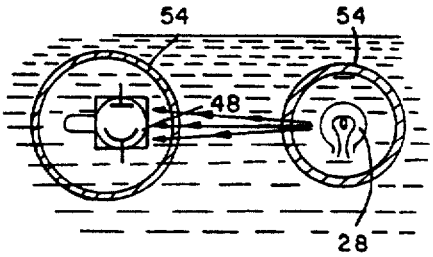

ULTRAVIOLET LIQUID PURIFICATION SYSTEM

Matter enclosed in heavy brackets [ ] appears in the original patent but forms no part of this reissue specification; matter printed in italics indicates the additions made by reissue.

BACKGROUND OF THE INVENTION

This invention relates to the purification and/or sterilization of fluids and in particular to the use of ultraviolet ray emissions for sterilization of fluids.

Conventional ultraviolet germicidal purification systems generally comprise a purification chamber having a plurality of ultraviolet lamps applying germicidal ultraviolet light radiation to the liquid flowing through said chamber. The ultraviolet radiation intensity and the total ultraviolet radiation dosage thus imparted to the liquid are respectively a function of number of ultraviolet lamps, the radiation intensity of each lamp and the exposure time. Accordingly, in order to control the ultraviolet radiation dosage being administered to the fluid, it is essential to monitor the operation of each ultraviolet lamp in the purification chamber. Such monitoring is particularly important where large flow rates of liquid are being handled such as in water purification systems.

Prior liquid purification systems comprised tanks each of which typically had a capacity of about 30–40 gpm connected in parallel in order to treat larger volumes of water. Such systems required complicated piping manifolds, specialized hydraulic controls to ensure equal flow rates through the respective tanks, which caused substantial pressure loss through the overall system. Furthermore, with increasing capacity thereof, such systems incorporated large numbers of ultraviolet lamps which made it difficult to monitor the radiation outputs thereof.

In the system of the present invention, a simple large purification chamber is provided [becoming] *with* banks of ultraviolet lamps distributed therein whereby large volumes of liquid may be treated without the need for piping manifolds, and specialized hydraulic controls as in the prior systems which required a flow control device for each of the several tanks. As a result, in the system of the present invention, large volumes of liquid may be treated without incurring significant pressure losses due to restrictions in flow.

Furthermore, in the system of the present invention dosage administered to the fluid in the chamber may be easily and selectively varied by switching on selected banks of ultraviolet lamps in accordance with the flow rate through the purification chamber, thereby conserving energy and ultraviolet lamp usuage.

Furthermore, in the system of the present invention, the ultraviolet lamp radiation sensors may be movably located within the chamber and selectively oriented to detect the level of ultraviolet radiation from selected lamps at various locations.

It is therefore an object of the present invention to provide a system for monitoring the operation of ultraviolet lamps in a fluid purification chamber.

It is a further object of the present invention to provide a monitoring system of the [characher] *character* described which monitors the ultraviolet radiation dosage imparted to the liquid being treated and the operative condition of each of said lamps and the ultraviolet transmission quality of the fluid passing through said purification chamber.

It is another object of the present invention to provide a monitoring system of the character described which provides an automatic alarm and fail-safe protection in the event of malfunction or failure in any of said ultraviolet lamps.

It is yet a further object of the present invention to provide a monitoring system of the character described which is operative to locate the particular [lamps(s)] *lamps(s)* which malfunctions or fails.

SUMMARY OF THE INVENTION

In accordance with the principles of the present invention, there is provided an ultraviolet liquid purification system comprising an ultraviolet purification chamber having liquid inlet and outlet parts and means for producing ultraviolet radiation located within said chamber operative to irradiate liquid in said chamber. There is further provided ultraviolet radiation sensor means for detecting the intensity level of the ultraviolet radiation produced by said ultraviolet radiation means and indicator means operative in response to said radiation sensor means to produce an indicator signal corresponding to said detected radiation intensity level.

Further objects, features and advantages of this invention will become apparent from a consideration of the following description, the appended claims and the accompanying drawings in which:

BRIEF DESCRIPTION OF THE DRAWINGS

FIG. 1 is a front perspective view of the purification chamber of a fluid purification system in accordance with the present invention;

FIG. 2A and 2B are schematic diagrams showing the in-place cleaning system for the ultraviolet purification chamber in FIG. 1;

FIG. 3A is a perspective schematic illustration of one of the quartz jacket of FIG. 1 showing how the ultraviolet photocell is mounted therein;

FIG. 3B is a section view taken along the line 3B—3B of FIG. 3A;

DETAILED DESCRIPTION OF THE INVENTION

Figure 2B:
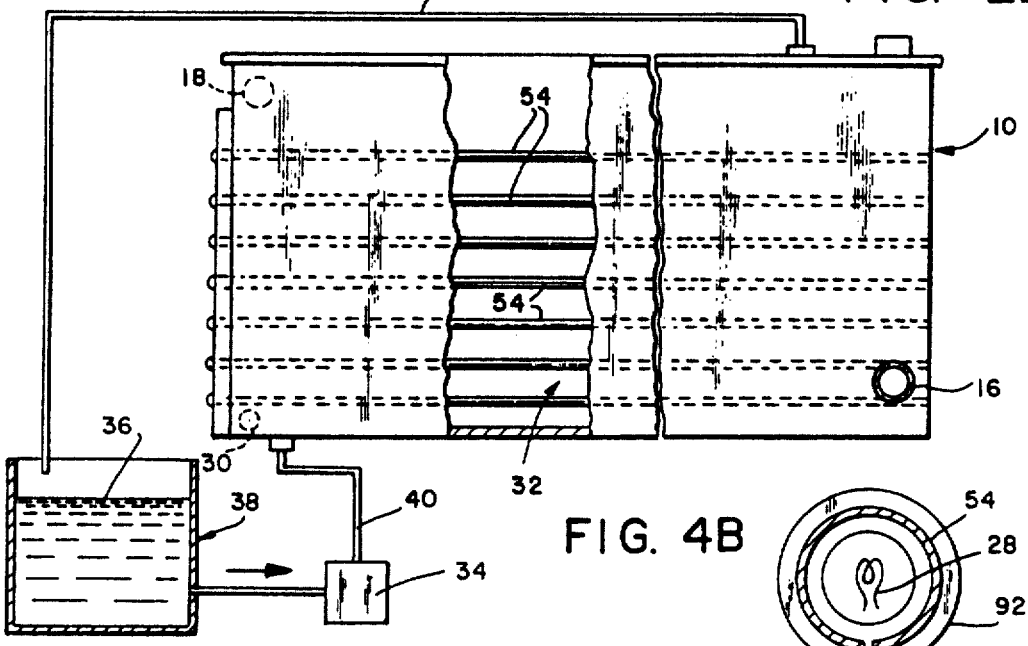

Referring to the drawings, and in particular to FIG. 1 thereof, a rectangular liquid purifier tank 10 comprises sidewalls, 12, 14 which are selectively provided with inlet and outlet ports 16 and 18 for circulation of liquid, such as water, through tank 10, the water line [20]

normally reaching the level of outlet port 18. Tank 10 further comprises a floor wall 22 and a top wall 24 including a transparent cover door 25 enclosing banks of ultraviolet (UV) radiation lamps 28 throughout the interior of chamber 32 as shown in greater detail in FIGS. 2B, 4A and 4B. A drain port 30 is provided in sidewall 14. The liquid to be treated, e.g. water, is caused to flow through the tank plenum chamber 32, where it is exposed to the germicidal energy emitted by ultraviolet lamps 28.

Figure 5:
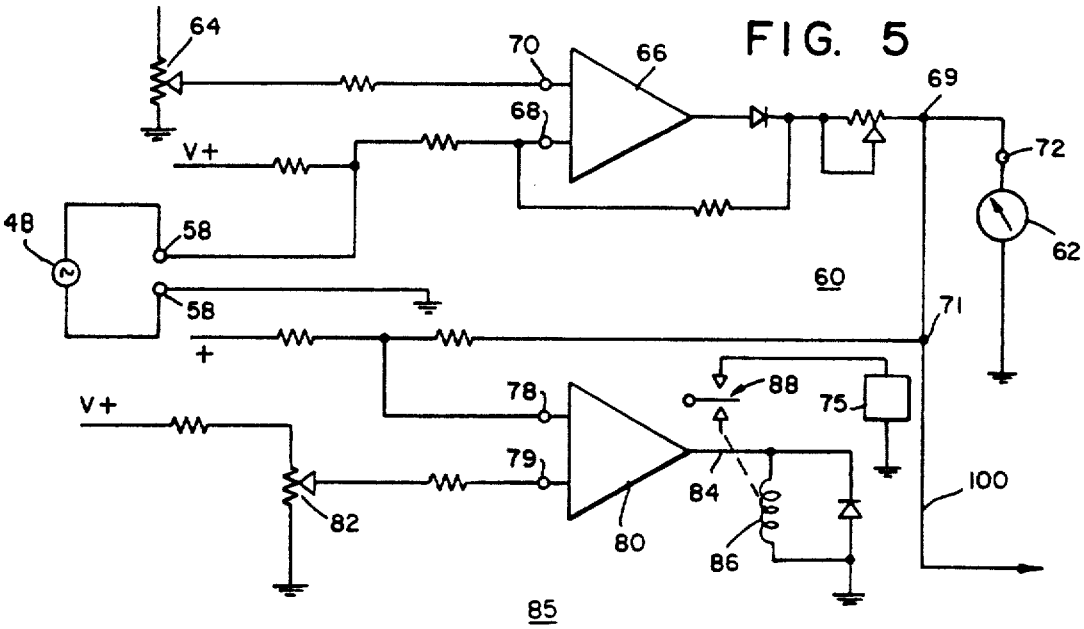
FIG. 5 is an electrical schematic diagram of the monitoring circuit for monitoring the transmission of UV energy through the fluid under treatment in the purification chamber of FIG. 1.
Figure 6:
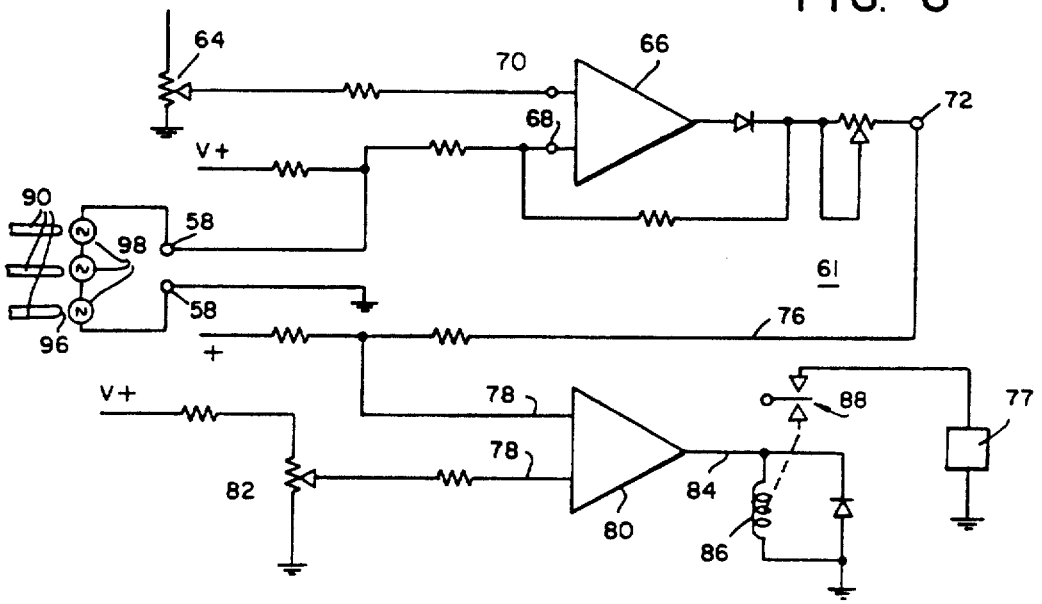
FIG. 6 is an electrical schematic diagram of a lamp monitoring circuit operative to detect the conducted light output of a plurality optical fibers respectively connected to corresponding ultraviolet lamps.

The ultraviolet energy dosage, imparted to the water, and hence the germicidal effect thereof, is a direct function of the intensity of the ultraviolet light energy produced by lamps 28, which, in turn, is proportional to the number of lamps and the exposure time of the liquid to the ultraviolet energy dosage. In order to ensure that an adequate ultraviolet germicidal energy is being delivered to the water under treatment, the apparatus of the present invention is provided with means for continuously monitoring the intensity of the ultraviolet light energy emitted by lamps 28, locating the particular lamp, if any, which has failed and actuating an appropriate alarm in such event, as hereafter described in greater detail. Thus, the monitoring system of FIG. 6 is operative to detect failure of any particular lamp 28, while the monitoring system of FIG. 5 is operative to detect the magnitude of the UV energy delivered through the liquid under treatment, which in turn is a function of the UV emission of the lamps, the absorption loss of UV energy due to coating build-up on the quartz jacket over lamps 28, and the optical density of the liquid under treatment.

Referring to FIG. 1, in many applications, a flow rate of about 0.2 gallons per minute per inch of length of the ultraviolet lamps 28, with a minimum retention time of 15 seconds assures an adequate ultraviolet dosage. Plenum chamber 32, which may be designed to operate either on a gravity flow or pressure system, may be provided with baffles (not shown) or similar known devices for controlling the flow of liquid in accordance with the aforementioned flow rate requirements. Ultraviolet lamps 28 may be located in tank 10 either perpendicular or parallel to the direction of flow, as required.

The ultraviolet lamps 28 are grouped i.e. wired in banks, so that selected banks of lamps 28 may be selectively turned on or off, depending on the fluid flow rate to selectively vary the disinfecting capacity of purifier tank. Thus, by way of example only, a liquid flow rate of 3000 gpm may require a total of 252 ultraviolet lamps 28. In this case, the lamps 28 would be wired so that a flow rate of 1000 gpm a bank of 84 lamps 28 would be turned on, for a flow rate of 2000 gpm two 84 lamp banks, i.e. a total of 168 lamps would be turned on, and for a flow rate of 3000 gpm three banks of 84 lamps, i.e. a total of 252 lamps would be turned on.

Electrical elapsed operation time indicators (not shown) may be provided for each of said lamp banks to facilitate timely replacement of the lamps 28 in the various banks and to achieve maximum utilization of lamp life.

As indicated hereinabove, in order to ensure that the fluid being treated is being subjected to an adequate ultraviolet energy dosage, it is essential to promptly detect any drop in such administered dosage due either to the formation of an ultraviolet energy absorbing coating on the lamp 28 or its quartz protective tube, to a drop in voltage at, or failure of a lamp 28.

In the system of the present invention, an in-place cleaning system, shown in FIGS. 2A and 2B serves to remove the ultraviolet energy absorbing coatings which form on the quartz jackets and the internal surfaces of purification chamber 32 without dismantling tank 10. Referring to FIGS. 2A and 2B, the cleaning process in accordance with the principles of the present invention comprises the following procedure. First, the normal flow of water through purification chamber 32 is interrupted by closing inlet and outlet ports 16 and 18 respectively by means of isolating valves (not shown), and tank 10 is drained of water. Cleaning solution 36 from cleaner storage tank 38 is then pumped by means of pump 34 into purification chamber 32 and circulated through chamber 32 and back to cleaning solution storage tank 38 through circulation feed line 40 and return line 42 for a suitable period of time. In order to ensure that adequate cleaning has been achieved, compressed air may be introduced into chamber 32 by an air inlet port (not shown) creating a fine stream of bubbles which produces a scrubbing and cleaning action on the surfaces of the quartz tubes 54 as well as the interior walls of purification chamber 32. It is understood that ultrasonic cavitation may be used instead of compressed air in order to produce the required scrubbing action. As a measure of preventative maintenance and improved UV efficiency, the aforementioned compressed air process may be employed continuously to eliminate the need for periodic cleaning and shutdown.

The UV intensity monitoring system for detecting the UV emission from the lamps 28, the UV absorption loss due to coating build-up on the quartz jacket 54 of the lamps 28 and the deterioration in the optical density of the liquid under treatment is shown in FIG. 3A, 3B and 5. Referring to FIGS. 3A and 3B, each photocell 48 is mounted in an acrylic holder 50 mounted on a connecting rod 52 which is slid into a quartz tube jacket 54 which is positioned intermediate several adjacent lamps 28 and a photocell 48 is oriented to receive ultraviolet light transmission through the liquid being treated. Photocell 48 may be slidably positioned along the length of connecting rod 52 and may be rotatably adjusted through 360° so as to provide selective monitoring of selected adjacent lamps 28. Each photocell 48 is electrically connected via a lead 56 extending through rod 52 to its own electrical monitoring circuit 60 at the input terminals 58 thereof shown in FIG. 5.

As previously indicated, the magnitude of the ultraviolet energy detected by photocells 48 is a function of the ultraviolet energy emission by the corresponding lamps 28, the coating build-ups of the lamp jacket 54 and the optical density, i.e. ultraviolet energy transmission quality, and hence the state of purity, of the fluid flowing therepast. These parameters are measured by means of a plurality UV monitoring circuits 60 shown in FIG. 5, each having a pair of input terminals 58 for connection of each of said photocells 48. Each UV monitoring circuit 60 comprises a comparator circuit in which the resistance of photocell 48 (which is a function of the ultraviolet energy impinging thereon), and hence the voltage thereacross is compared with a reference voltage corresponding to optimum operating condition of the ultraviolet lamp 28 and optimum quality of the fluid being purified. Thus, the comparator circuit comprises a potentiometer 64 for setting the reference voltage corresponding to the aforementioned optimum fluid quality and lamp UV output conditions. The voltage across photocell 48 applied at input terminals 58 is fed to D.C. amplifier 66 at one of its input terminals 68 while the reference voltage is fed into the other input terminal 70 of D.C. amplifier 66 which compares the two input signals and produces an output signal at its output terminal 69 corresponding to the difference therebetween. This output signal is applied via lead 71 to alarm circuit 85 at the input terminal 78 of differential amplifier 80.

Amplifier 80 is operative to compare the aforementioned photocell signal applied at its input terminal 78 with the alarm reference signal provided by potentiometer 82 applied at input terminal 79, and if the photocell signal is sufficiently high, the output signal of amplifier 80 at its terminal 84 will energize relay solenoid coil 86 to operate relay contacts 88 to actuate a suitable alarm 75. Furthermore, a D.C. meter 62 may be connected to output terminal 69 to provide an analog indication of the UV intensity measured by photocell 48.

The alarm signal output at output terminals 84 may be utilized to automatically initiate the in-place cleaning system described above thereby providing an important preventative maintenance feature to the present system. Thus, the electrical output signal at terminals [83] *84* may be electrically connected to a suitable electrically controlled (e.g. solenoid operated) valve 102 (FIG. 2A) whereby the in-place cleaning operation would be initiated when the photocells 48 indicate that the fluid under treatment is not obtaining sufficient ultraviolet energy. If, however, the alarm signal at output terminals 84 exceed a preselected danger level; such signal may be employed to automatically shut-off the entire system and cause alarm 75 to emit a danger bell (not shown) or similar signal to alert the operator of the existence of a serious malfunction of the system.

Figure 4B:
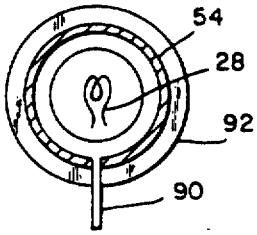
FIG. 4B is a section view taken along the line 4B—4B of FIG. 4A.
Figure 4A:
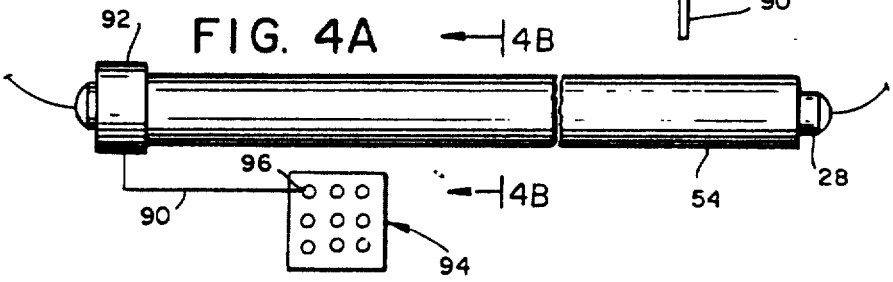
FIG. 4A is a side elevational view of an ultraviolet lamp in said fluid purification systems showing the connection of the fiberoptic light conductor to the quartz jacket.

As shown in FIGS. 4A, 4B and 6 the system of the present invention also provides means for monitoring each of the ultraviolet lamps 28 on an individual basis, i.e. to determine whether an ultraviolet lamp 28 has burned out and if so to locate the particular lamp 28 in question. In addition to the ultraviolet photocell detector 48, a light-conducting fiber 90 is connected at one end thereof to the quartz jacket 54 of an ultraviolet lamp 28 through the neoprene sleeve 92, whereby the input endface of said optical fiber 90 faces and is illuminated by ultraviolet light from tube 28. The other end of fiberoptic member 90 is connected to display panel 94 whereby the other (i.e. output) endface 96 of member 90 appears at the front face of display panel 94. Display panel 94 is suitably marked to identify the output endfaces of the various fiberoptic members connected to the various ultraviolet lamps. If an ultraviolet lamp 28 is on, light from the lamp 28 is conducted by fiberoptic member 90 to its output endface 96 at display panel 94. If a lamp 28 burns out of fails, its corresponding fiberoptic member output endface 96 will be dark thus identifying the particular lamp 28 in question.

Referring to FIG. 6 additional photocells 98 are located adjacent the output faces 96 of fibers 90 to detect a lack of light produced by a particular fiber 94 corresponding to a particular lamp 28. The series arrangement of photocells 98 is connected to the input terminals 58 of a comparator circuit similar to that of FIG. 5. Accordingly, failure of a single lamp 28 will cause a lack of light at its corresponding fiberoptic endface 96 producing a substantial drop in the resistance across input terminals 58. As explained above, such drop in the resistance and consequently the voltage applied at the input terminals 58 of comparator circuit 61 will produce a signal at its output terminal 72 to actuate alarm 77 connected thereto. As a result, the operator will be alerted to check display panel 94 to locate the particular lamp 28 which has failed.

Figure 7:
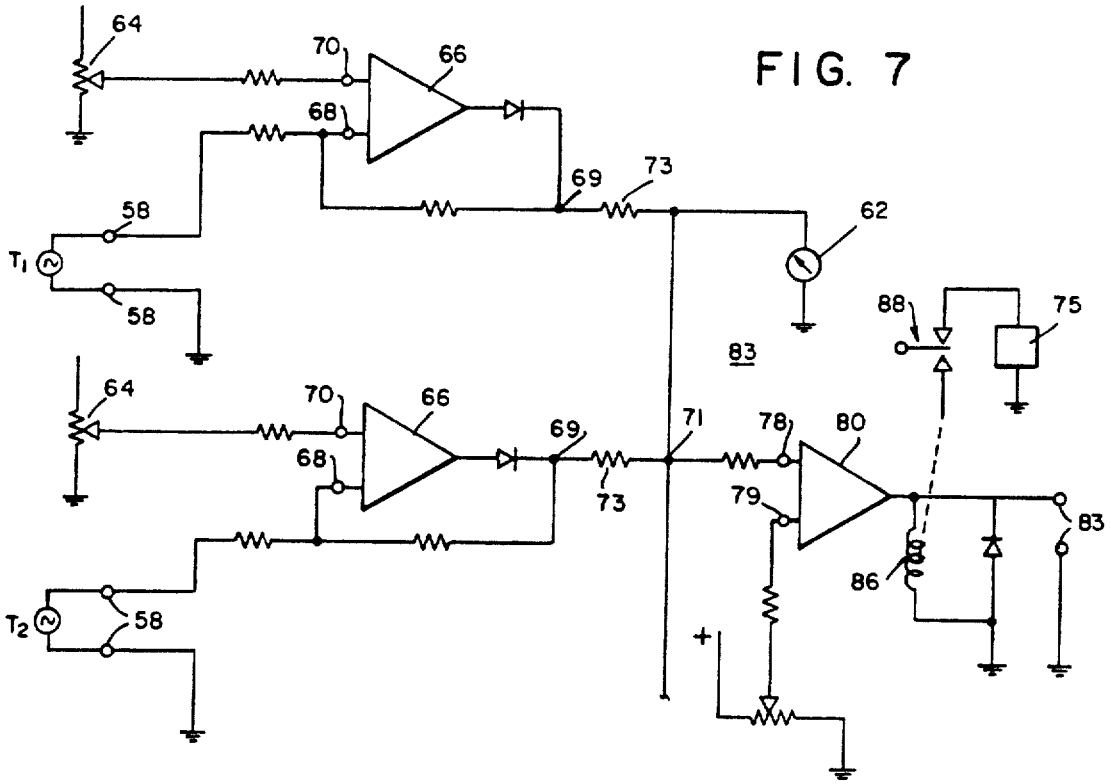
FIG. 7 is an electrical schematic diagram of an alternate UV lamp monitoring circuit utilizing toroids for detecting the operating condition of the various ultraviolet lamps.

It is understood that circuits other than monitoring circuit 61 of FIG. 6, may be employed for detecting the light output of lamps 28. Thus, a toroid may be connected to the secondary winding of the ballast (not shown) for each lamp 28, the current is such toroid corresponding to the electrical operation output of the lamps 28. Each of such toroids $T_1$, $T_2$, etc. may be respectively connected to the various branches of a summing network of the type illustrated in FIG. 7 and the summed voltage signal may be applied to an alarm circuit similar to circuit 85 of FIG. 5. Thus, each of the branches and alarm circuit 83 is similar to monitoring circuit 60 and alarm circuit 85 of FIG. 5 and hence corresponding elements thereof are provided with similar identifying numerals. Alternately, the various secondary windings of the lamp ballasts may be directly wound on the primary side of a toroid to produce a current in the secondary winding of the toroid which corresponds to the sum of currents in the ballast secondary windings, with the toroid secondary winding being applied to a suitable alarm circuit such as alarm circuit 85 of FIG. 5.

Although the invention has been described with respect to a particular embodiment thereof, it is to be understood that such embodiment is merely illustrative of the application of the principles of the invention. Numerous modifications may be made therein and other arrangements may be devised without departing from the spirit and scope of the invention.

What is claimed is:

1. An ultraviolet liquid purification system comprising an ultraviolet purification chamber having liquid inlet and outlet ports; a plurality of ultraviolet lamps located within said chamber and operative to irradiate liquid in said chamber; a plurality of ultraviolet sensors located to detect ultraviolet radiation transmitted through said liquid from said ultraviolet lamps; a plurality of light conducting fibers for monitoring the operation of said ultraviolet lamps each of said light conducting fibers having its endface located in close proximity with a corresponding ultraviolet lamp to directly receive light radiation therefrom; ultraviolet transmission indicator means operative in response to said ultraviolet sensors to produce an ultraviolet transmission indicator signal corresponding to the detected ultraviolet radiation transmitted through said liquid; and lamp condition indicator means associated with said light conducting fibers and operative to produce a lamp condition indicator signal corresponding to the light emitted by said lamps.

2. An ultraviolet liquid purification system as defined in claim 1 wherein each of said ultraviolet sensors comprises an ultraviolet photocell operative to produce an ultraviolet energy level output signal whose magnitude corresponds to the ultraviolet energy received therefrom.

3. An ultraviolet liquid purification system as defined in claim 2 wherein said ultraviolet transmission indicator means comprises means to produce an output alarm signal when said ultraviolet energy level output signal is less than a first preselected level.

4. An ultraviolet liquid purification system as defined in claim 1 wherein said lamp condition indicator means includes a display panel, each of said light conducting fibers having its output endface located on said display panel operative to display light conducted from a respective ultraviolet lamp, to thereby provide a visual indication of the light output of said respective ultraviolet lamps.

5. An ultraviolet liquid purification system as defined in claim 1 including a lamp monitoring circuit comprising a plurality of photocells respectively positioned opposite the corresponding output endfaces of said light conducting fibers, and comparator circuit means operative to produce an output alarm signal when the electrical output of said [photocell exceeds] *photocells is less than* a preselected level.

6. An ultraviolet liquid purification system comprising an ultraviolet purification chamber having liquid inlet and outlet ports; a plurality of ultraviolet lamps located within said chamber and operative to irradiate liquid in said chamber; a plurality of ultraviolet photocells located to detect ultraviolet radiation transmitted through said fluid from said ultraviolet lamps and operative to produce an ultraviolet energy level output signal whose magnitude corresponds to the ultraviolet energy received thereon; indicator means operative in response to said photocells to produce an indicator signal corresponding to the intensity level of said transmitted ultraviolet radiation, said indicator means including means to produce [an] *a first* output alarm signal when said ultraviolet energy output signal [exceeds] *is less than* a first preselected level; and an in-place cleaning system for cleaning the interior of said purification chamber comprising a feed line and a return line respectively connected to said purification chamber, means operative to drain the contents of said purification chamber, and pump means operative to circulate cleaning solution through said purification chamber via said feed line and return line.

7. An ultraviolet liquid purification system as defined in claim 6 wherein said in-place cleaning system includes means for agitating said cleaning solution in said purification chamber to produce a scrubbing action therein.

8. An ultraviolet liquid purification system as defined in claim 6 including valve means operative in response to said first *output* alarm signal to activate said in-place cleaning system.

9. An ultraviolet liquid purification system as defined in claim 6 wherein said indicator means is operative to produce a second output alarm signal when *the difference between* said ultraviolet energy level output signal [is less than] *and the first preselected level exceeds* a second preselected level.

10. An ultraviolet liquid purification system as defined in claim 6 including shut-off means operative in response to said second output alarm signal to shut-off said liquid purification system.

11. An ultraviolet liquid purification system comprising an ultraviolet purification chamber having liquid inlet and outlet ports; a plurality of *banks of* ultraviolet lamps located within said chamber and operative to irradiate liquid in said chamber; a plurality of ultraviolet photocells located to detect ultraviolet radiation transmitted through said fluid from said ultraviolet lamps and operative to produce an ultraviolet energy level output signal whose magnitude corresponds to the ultraviolet energy received thereon; indicator means operative in response to said photocells to produce an indicator signal corresponding to the intensity level of said transmitted ultraviolet radiation, said indicator means including means to produce an output alarm signal when said ultraviolet energy output signal [exceeds] *is less than* a first preselected level; and a lamp monitoring circuit comprising means for detecting the electrical power flow in said ultraviolet lamps respectively.

12. An ultraviolet liquid purification system as defined in claim 11 wherein said means for detecting the electrical power flow comprises a plurality of toroids respectively connected to the secondary windings of the ballasts of said ultraviolet lamps respectively.

*13. An ultraviolet liquid purification system comprising an ultraviolet purification chamber having liquid inlet and outlet ports; a plurality of banks of ultraviolet lamps located within said chamber and operative to irradiate liquid flowing through said chamber; a plurality of ultraviolet photocells located in said chamber and positioned to detect ultraviolet radiation transmitted through said fluid from said ultraviolet lamps and operative to produce an ultraviolet energy level output signal whose magnitude corresponds to the ultraviolet energy received at the photocells and wherein each bank includes at least one photocell; indicator means operative in response to said photocells to produce an indicator signal corresponding to the intensity level of said transmitted ultraviolet radiation, said indicator means including means to produce an output alarm signal when said ultraviolet energy output signal is less than a preselected level; and a lamp monitoring circuit comprising means for detecting the electrical power flow in said ultraviolet lamps respectively, locating failed ultraviolet lamps and activating an alarm upon failure of any lamp.*

* * * * *